(12) United States Patent
Jornéus et al.

(10) Patent No.: US 6,902,401 B2
(45) Date of Patent: Jun. 7, 2005

(54) METHOD AND ARRANGEMENT FOR AN IMPLANT SUPERSTRUCTURE

(75) Inventors: Lars Jornéus, Frillesås (SE); Göran Bjorn, Onsala (SE)

(73) Assignee: Nobel Biocare AB, Göteborg (SE)

( * ) Notice: Subject to any disclaimer, the term of this patent is extended or adjusted under 35 U.S.C. 154(b) by 168 days.

(21) Appl. No.: 10/169,313

(22) PCT Filed: Jan. 30, 2001

(86) PCT No.: PCT/SE01/00166

§ 371 (c)(1),
(2), (4) Date: Jul. 3, 2002

(87) PCT Pub. No.: WO01/54609

PCT Pub. Date: Aug. 2, 2001

(65) Prior Publication Data

US 2002/0192620 A1 Dec. 19, 2002

(30) Foreign Application Priority Data

Jan. 31, 2000 (SE) .............................................. 0000305

(51) Int. Cl.$^7$ ................................................. A61C 8/00
(52) U.S. Cl. ...................................... 433/173; 433/172
(58) Field of Search ................................ 433/172, 173, 433/174

(56) References Cited

U.S. PATENT DOCUMENTS

| | | | | | |
|---|---|---|---|---|---|
| 4,516,937 | A | * | 5/1985 | Bosker | 433/173 |
| 4,767,328 | A | * | 8/1988 | Branemark | 433/168.1 |
| 4,906,189 | A | * | 3/1990 | Knapp | 433/173 |
| 5,419,700 | A | * | 5/1995 | Sillard | 433/172 |
| 5,630,717 | A | * | 5/1997 | Zuest et al. | 433/172 |
| 6,250,924 | B1 | * | 6/2001 | Luotio | 433/173 |
| 6,305,938 | B1 | | 10/2001 | Brånemark | |
| 6,319,000 | B1 | | 11/2001 | Brånemark | |
| 6,382,975 | B1 | * | 5/2002 | Poirier | 433/173 |

FOREIGN PATENT DOCUMENTS

WO    97/49351    12/1997

OTHER PUBLICATIONS

C. Darle, Brånemark Novum—Minimized Treatment For Maximal Predictability Same–Day–Teeth®—A New Concept For Treating The Edentulous Mandible, Brånemark Osseointegration Center May 1999, pp. 3–14.
Brånemark et al., Brånemark Novum®: A New Treatment Concept for Rehabilitation of the Edentulous Mandible. Preliminary Results from a Prospective Clinical Folow–Up Study, 1999 B.C. Decker, Inc., Clinical Implant and Related Research, vol. 1, No. 1, pp. 2–16.

* cited by examiner

Primary Examiner—Ralph A. Lewis
(74) Attorney, Agent, or Firm—Eric J. Franklin

(57) ABSTRACT

A superstructure is included together with other components in a tooth prosthesis system, by means of which a tooth prosthesis is intended to be applied to a patient in a short application time, for example in one or only a few days. The superstructure (1) is designed with a bearing part (1b) which can cooperate with fixture members, and a tooth-prosthesis-supporting part, and the parts are designed with recesses for said securing members. The bearing part and the tooth-prosthesis-supporting part are integrated over at least most of their horizontal extents by means of the parts being produced from a common blank or a material composition using a treatment or method which gives a user-friendly outer shape and bevels on the unit or superstructure forming the parts.

37 Claims, 3 Drawing Sheets

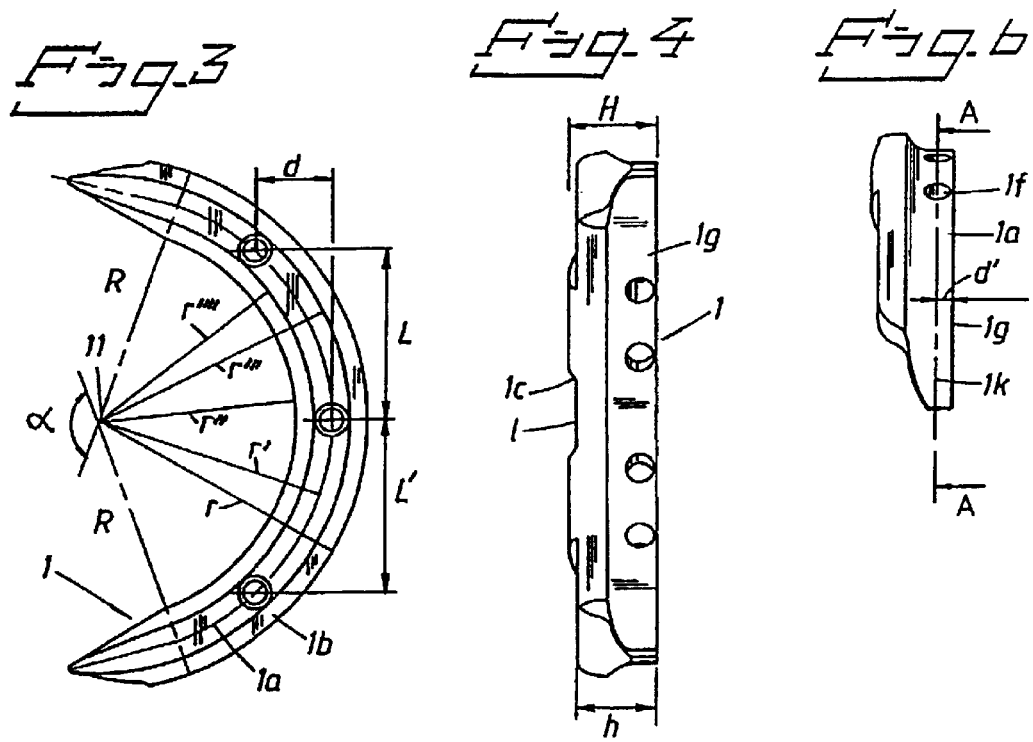
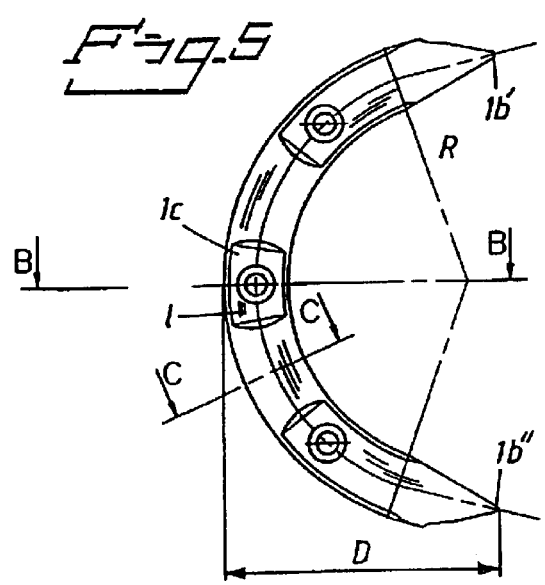

METHOD AND ARRANGEMENT FOR AN IMPLANT SUPERSTRUCTURE

FIELD OF THE INVENTION

The present invention relates to a method for producing a superstructure which is included in a tooth prosthesis system together with, inter alia, positioning members, drill guide sets, fixture guide sets and fixtures or fixture members, for example fixtures with associated spacer members, and securing members for anchoring the superstructure in the fixtures or fixture members, by means of which tooth prosthesis system a tooth prosthesis is intended to be applied (to a patient) at the time when, or a short time after, the fixtures have been applied (implanted) in the patient's jaw bone, for example on the same day or after just a few days. The superstructure can in this case be designed with a bearing part which can cooperate with the fixtures or fixture members, and a tooth-prosthesis-supporting part. The parts are designed with recesses through which the securing members extend upon said anchoring. The invention also relates to an arrangement in association with said superstructure.

BACKGROUND OF THE INVENTION

It is already known, for example from Swedish Patents 9602554-9 (506850) and 9602555-6 (506849), to provide such a tooth prosthesis system by means of which implantation and tooth prosthesis structuring can be executed in a very short time compared with the current times of 3 to 6 months. Reference is also made to the BRÅNEMARK NOVUM® system which is described for example in "Clinical Implant Dentistry and Related Research, Volume 1, Number 1, 1999" and the publication "Brånemark Osseointegration Center, May 99". The concept is also described in the "Manual for Clinical Investigation 1999". From the first-mentioned patent specification it is known to use a superstructure which expediently comprises a separate rail with securing members and a tooth prosthesis bridge which can be attached to the rail (see, for example, page 5, paragraph 4). The use of two matching upper and lower parts which are intended to bear against each other via a contact surface is also shown in detail in said "Manual".

SUMMARY OF THE INVENTION

In the field of dentistry there is an urgent need to reduce the number of parts and components and at the same time to simplify techniques of producing and using said parts and components. There are a very large number of components on the market, and every successful attempt at implementing tried and tested and novel methods for effective treatment using a reduced number of components is seen as a step forward not only from the purely technical point of view, but also from organizational and economic points of view. When fitting a tooth prosthesis, it is essential to have access to components which are easy to adapt to different individuals, and in this respect it is important to have access to components and parts which are not critical from, for example, the point of view of structural height. It is also important to be able to make changes to the implantation method as such without adversely affecting the final result. It is important to be able to shorten the treatment time for the patient and thus eliminate certain intermediaries without adversely affecting the final result. It is also important to be able to improve the purely esthetic effect of the implanted tooth prosthesis. The main object of the present invention is to solve all or some of these problems.

That which can principally be regarded as characterizing a method according to the invention is that the bearing part and the crown-supporting part are integrated over at least most of their horizontal extents, at the time of or in connection with the manufacture of the parts, by means of the parts being produced from a common blank or a material composition using a treatment or method which gives user-friendly outer shapes or bevels on the parts.

In further developments of the inventive concept, it is proposed that, at the time of manufacture, the tooth-prosthesis-supporting part is given a shape which, in the horizontal cross section of the superstructure, is narrower than the bearing part, and that the parts are in this case formed with an outside transition which forms a curved or arc-shaped transition between the parts. Moreover, at its end surfaces which can cooperate with the fixtures or fixture members, the bearing part can be given depressions with plane bottom surfaces which are opposite the end surfaces of the fixtures or fixture members. The plane bottom surfaces of the depressions are given surface areas which exceed the surface areas of the fixtures or fixture members at the parts of the fixtures or fixture members cooperating with said bearing part. Moreover, at the time of its manufacture, the crown-supporting part can be provided with a number of holes extending in the transverse direction. Said parts can be made of titanium or another tissue-compatible material or tissue-compatible alloy. In a preferred embodiment, the parts are designed with a relatively low height, for example a height of between 0.5 and 1.0 mm, preferably between 0.7 and 0.8 mm. In one illustrative embodiment, the unit made up of said parts is produced by machining of a blank with subsequent grinding and/or barrel-polishing of sharp edges and production of outer bevels which give said user-friendliness. In a further embodiment, the unit forming the parts can be produced by casting material which can be sintered and solidified, and by subjecting it to a sintering procedure, and by subsequent working of the outer shape to give said user-friendliness. Moreover, at its front parts, the unit forming the superstructure can be provided or covered with material forming the tooth prosthesis, for example acrylate or another synthetic material normally used in tooth prostheses. The recesses for the securing members can have diameters which are only slightly less than the width of the tooth-prosthesis-supporting part. At the time of its production, the unit forming the superstructure can be given an arc shape and, at the ends of the arc shape, there are parts with a first bevel which is arranged on the bearing part and which via a curved part merges with the lower surface of the tooth-prosthesis-supporting part, which in turn is curved up toward the outer edge of the tooth-prosthesis-supporting part via a second bevel.

That which can principally be regarded as characterizing an arrangement according to the invention is set out in the characterizing clause of the attached independent arrangement claim. Embodiments of the arrangement are set out in the subclaims linked to said independent claim.

By means of what is proposed above, which runs counter to the avenues already followed in the prior art and thus opens up new approaches in this field, it is possible to eliminate an intermediate stage in the treatment by omitting the mutual relating and adapting of two cooperating parts. The material-working time in machine-working or "milling" of a blank can be substantially reduced and rendered less expensive. Considerable freedom of choice of the structure of the components can be allowed, and user-friendly and esthetically pleasing tooth prostheses can be obtained.

BRIEF DESCRIPTION OF THE DRAWINGS

A presently proposed embodiment of a method and of an arrangement according to the invention will be described below with reference to the attached drawings, in which:

FIG. 3 shows, in a horizontal view from above, the superstructure in one structural illustrative embodiment, FIG. 4 shows the superstructure according to FIG. 3 from the inside and in a side view, FIG. 5 shows the superstructure according to FIGS. 3 and 4 from below, FIG. 6 shows the superstructure according to FIG. 4 from the side.

DETAILED DESCRIPTION OF PREFERRED EMBODIMENTS

Figure 1:
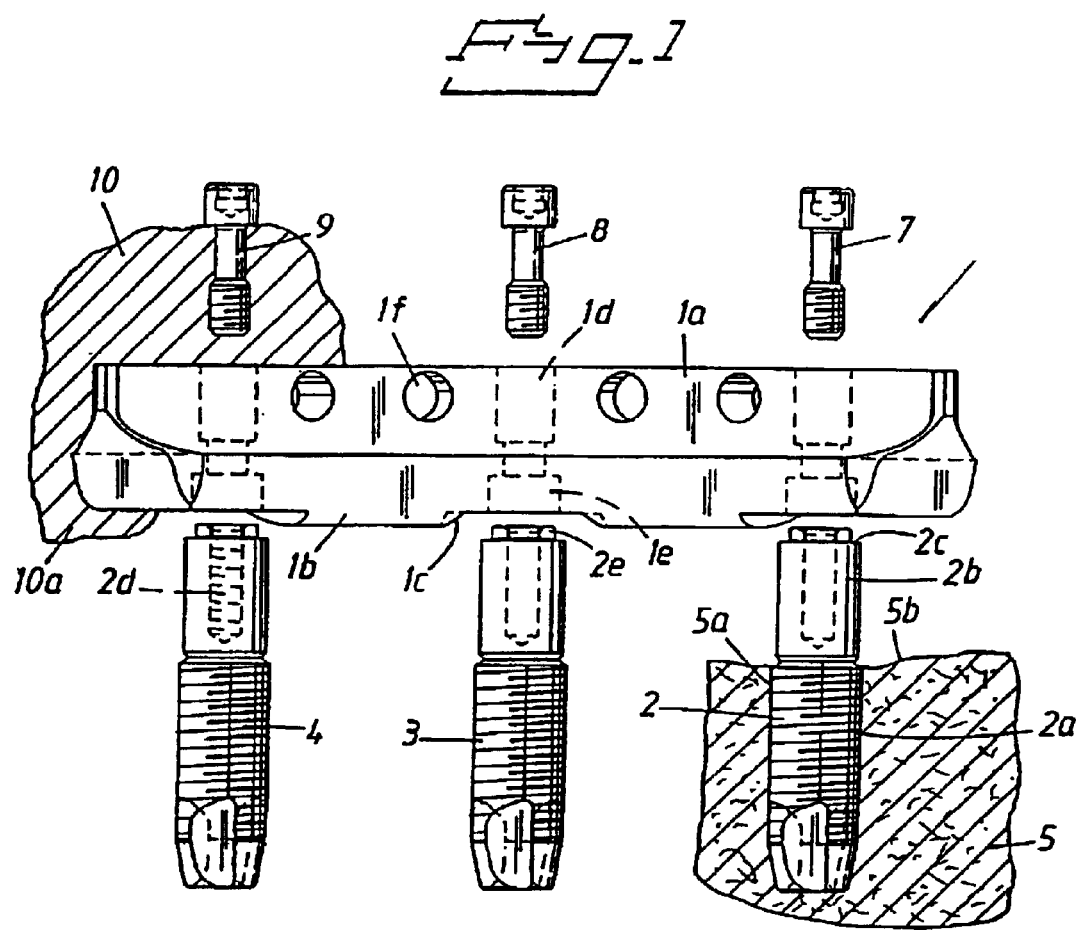
FIG. 1 shows, from the rear and in partial cross section, a superstructure and three implants or fixtures set in relation to it, with spacer members, securing screws for anchoring the superstructure in the implant, and areas of dentine, for example in the lower jaw of a human.

In FIG. 1, a superstructure is shown by 1. The superstructure comprises a tooth-prosthesis-supporting part $1a$, and a bearing part $1b$ which can cooperate with fixtures 2, 3 and 4. The parts $1a$ and $1b$ form a common unit, integrated along the greater part of their imaginary surfaces facing each other, cf. the surfaces of the separate parts according to the prior art. Each fixture is built in a manner known per se and can comprise an implant part which is provided with a thread $2a$, by means of which the implant or fixture can be screwed down into a hole in partially indicated dentine (jaw bone) 5, preferably the lower jaw of a patient. The hole in the jaw bone is indicated by $5a$ in FIG. 1. At its upper end, the fixture or implant screwed down into the actual dentine or jaw bone has a spacer member which, in the incorporated state of the implant, is intended to extend above a jaw bone surface $5b$. The implant can be of the self-tapping type, and for examples of implants reference can be made to Swedish patent application 9900822-9 with date of filing Mar. 9, 1999. The upper end of the implant or the spacer member $2b$ has a plane end surface $2c$. The bearing part $1b$ is provided with depressions $1c$ with plane bottom surfaces against which the upper surfaces $2c$ of the implants are intended to bear. The unit 1 can be anchored in the implant by means of anchoring screws 7, 8 and 9. The anchoring screws extend in recesses $1d$ through the unit 1 and each implant or spacer member is provided with a thread $2d$, in which the respective screw or in which the respective anchoring member 7, 8 or 9 can be anchored. This anchoring is therefore done in a manner known per se. The upper part $1a$ is provided with a number of through-holes $1f$ which extend in the transverse direction of the upper part and which are used for holding the tooth-prosthesis-supporting part $1a$, as is symbolically indicated by 10. On its upper side, each implant or each spacer member is provided with a hexagon $2e$ which is arranged to protrude into a recess $1e$ with a shape corresponding to the hexagon or with a shape locking the hexagon. The hexagon $2e$ can be of another shape. The tooth prosthesis material 10 can be designed with a part $10a$ which extends well above and covers both the part $1a$ and the part $1b$, thus affording advantages from the esthetic point of view.

Figure 2:
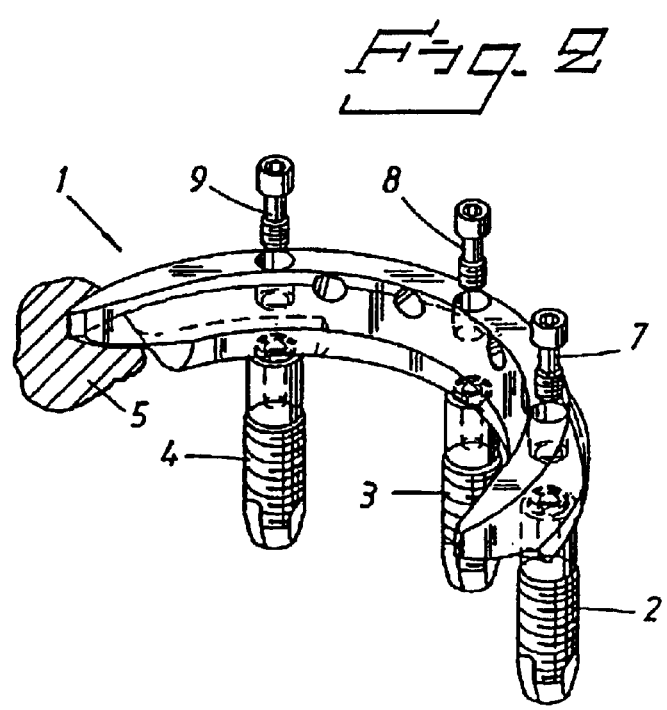
FIG. 2 shows, in a perspective view obliquely from above right/from the rear, the superstructure with the implants/fixtures and the securing screws according to FIG. 1.

FIG. 2 is intended to show the design or curve of the superstructure in a horizontal plane, which design or curve is arc-shaped and has an arc shape or curve following the curvature of the symbolically indicated dentine 5. The figure shows the application of the implants 2, 3 and 4 and the securing screws 7, 8 and 9 in said arc shape.

In FIG. 3, the superstructure is shown with its parts $1a$ and $1b$, from which it will be seen that the part $1a$ has a narrower design than the part $1b$. In the example shown, the arc shape is substantially circular and the center is indicated by 11. A radius r to the outer edge of the part $1b$ is of the order of size of 23 mm. A radius r' to the circular center line of the parts $1a$ and $1b$ is of the order of size of 20 mm. A radius r" to the arc-shaped inner edge of the lower part is chosen at about 17 mm. The radii r''' and r'''' to the arc-shaped outer and inner sides, respectively, of the part $1a$ are chosen at about 21 mm and 18 mm, respectively. In the horizontal plane shown, the distances L, L' between the securing member recesses $1d$ are chosen at about 14.75 mm. A distance d in the radial direction between the recesses is chosen at about 6.5 mm. In FIG. 3, a first angle $\alpha$ has been indicated for the radius R from the rearward/inward narrowing of the part $1b$. Said narrowing starts at a value of about 140° at said angle $\alpha$. Said start of narrowing at the radii R is related to the inner surface of the part $1b$. A narrowing is also present for the outer surface of the part $1b$ and the last-mentioned narrowing starts at a greater angle $\alpha$ (not shown in the figure for reasons of clarity).

In FIG. 4, the height of the superstructure is indicated by H. This height can be between 5 and 8 mm, for example about 6.5 mm. FIG. 4 also shows the size of the depression $1c$, or rather a height h between an underside $1g$ of the superstructure and a bottom surface of the respective depression. Dimension h is about 0.5 mm less than the height H. The bottom surface of the depression $1c$ has a surface area 1 which exceeds the corresponding surface area of the surface $2c$ of the implant concerned (cf. FIG. 1).

In FIG. 5, the depressions $1c$ on the part $1b$ are shown from below. The surface area extents 1 are again shown. As will be seen from the figure, the surface area of the depressions is narrower at the inner surface of the part $1b$ than at the outer surface of the same part. FIG. 5 also shows that, at said radius R, the part $1b$ merges at its ends into a narrowed shape, in the horizontal section according to FIG. 5, toward the points $1b'$ and $1b''$ of the superstructure. The total depth of the superstructure is indicated by D and is chosen at about 25.7 mm.

FIG. 6 shows the positions of the holes $1f$ on the part $1a$, a distance d' between the lower surface $1g$ and the center line $1k$ of the hole having been chosen at about 1.5 mm.

Figure 7:
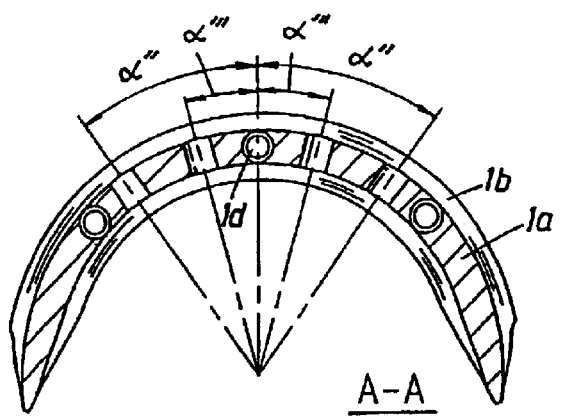
FIG. 7 shows said superstructure in cross section along A—A in FIG. 6.

FIG. 7 shows the mutual relationships of the holes and their relationship to the central recess $1d$. The angle between the recess $1d$ and each through-hole is indicated by means of the angles $\alpha''$ which can be chosen at about 35°. The distance between the inner transverse holes and the recess $1d$ is indicated by the angles $\alpha'''$ and in the present case has been chosen at about 15°. The parts $1a$ and $1b$ are also indicated in this case.

Figure 8:
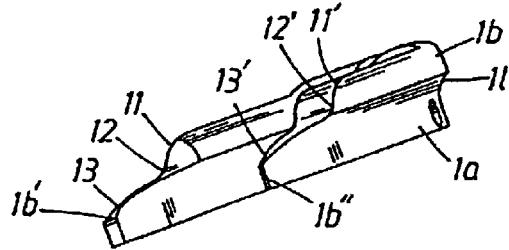
FIG. 8 shows the superstructure from the side and slightly turned in relation to FIG. 6.

FIG. 8 shows the terminal transition between the parts $1a$ and $1b$ at the ends $1b'$ and $1b''$. Said transitions are characterized by a first phase 11, 11' which merges into a curved transition part or 12, 12' and is thereafter finished by a further upswing phase 13, 13'.

Figure 9:
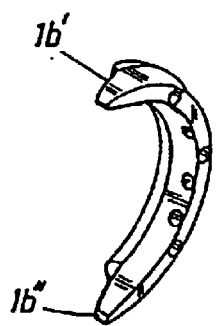
FIG. 9 shows the superstructure in a perspective view, obliquely from above left, FIG. 10, in cross section along B—B in FIG. 5, shows the design of the bearing part and the crown-supporting part at one of the recesses for the securing members.

FIG. 9 shows said phases (although not marked in the figure) at said ends 1b' and 1b".

Figure 10:
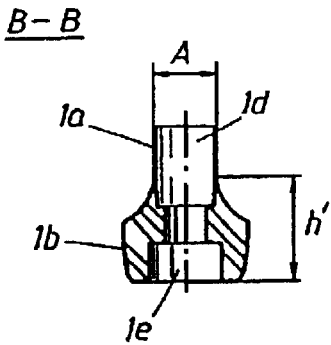
Figure 11:
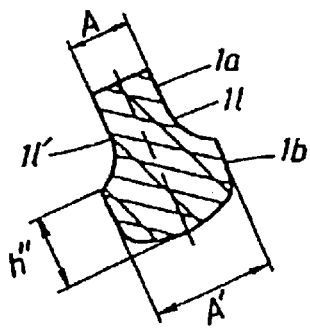
FIG. 11 shows the cross section of the unit along C—C in FIG. 5.

FIGS. 10 and 11 show in detail the cross sections of parts 1a and 1b. The part 1a has a width of about 2.8 mm in the depth direction which is indicated by A. The width or depth of the part 1b is indicated by A' and is chosen at about 5.5 mm. The part 1b at the hole or recess 1d of the securing member is indicated by 1h' and assumes a value of about 3 mm. The corresponding height h" at the position alongside the hole 1d, i.e. the position according to FIG. 11, assumes values of about 3.2 mm. FIG. 11 also shows the outside transitions 1l, 1l'. Said transitions are arc-shaped or curved. FIG. 8 too shows the transition 1l.

The superstructure can be used in combination with positioning members, drill guide sets and fixture guide sets of the type shown in Swedish patent specification 9602554-9 (506850) mentioned at the outset. These members are therefore not described in detail here, but reference is made to the embodiments according to said patent.

The superstructure can be produced by means of machining equipment in the form of milling members. After milling, the milled superstructure is surface-treated, for example by grinding equipment. Such equipment is already well known.

Alternatively, a material composition or a material powder can be introduced into a mold for casting the superstructure. The superstructure thereby formed in the mold is sintered in an oven or can be made of a material that can solidify. The production equipment can in this case too consist of types known per se and will therefore not be described in detail here.

By means of the above embodiment of the superstructure, the latter does not therefore have to take part in the covering function for the implants implanted in the dentine or jaw bone, and instead these implants or their ends can be exposed or uncovered during tooth prosthesis application to the unit forming the superstructure. This function affords the considerable advantage that adjustment between two different parts does not need to take place and that the covering function for the implant ends is not itself necessary in accordance with the proposal of the invention.

According to FIG. 1, the front parts of each implant in accordance with the above have cutting edges 2f which provide a direction-stabilizing function during screwing into the dentine, irrespective of any inhomogeneity of the latter. The design and function of the cutting edge are described in the abovementioned patent application.

The invention is not limited to the embodiment described above by way of example, and instead it can be modified within the scope of the attached patent claims and the inventive concept.

What is claimed is:

1. A method for producing a superstructure for use in a tooth prosthesis system together with fixtures and securing members for anchoring the superstructure in the fixtures, the tooth prosthesis system being designed to be applied to a patient in a short application time, the method comprising:

designing the superstructure with a unitary member comprising a bearing part operative to cooperate with the fixtures, and a tooth prosthesis-supporting part;

designing the bearing part and the tooth prosthesis-supporting part with recesses through which the securing members extend upon said anchoring; and providing the superstructure with an arc shape;

providing ends of the arc shape with a first bevel arranged on the bearing part that merges with a lower surface of the tooth prosthesis supporting part via a curved surface, the lower surface of the tooth prosthesis supporting part being curved up toward an outer edge of the tooth prosthesis supporting part via a second bevel; and integrating the bearing part and the tooth prosthesis-supporting part over at least most of their horizontal extents.

2. The method according to claim 1, wherein the bearing part and the tooth prosthesis supporting part are integrated by producing the parts from a common blank or a common material composition.

3. The method according to claim 1, further comprising:
providing the bearing part and the tooth prosthesis supporting part with user-friendly outer shapes or bevels.

4. The method according to claim 1, wherein the bearing part and the tooth prosthesis supporting part are integrated at the time of or in connection with their manufacture.

5. The method according to claim 1, wherein the fixtures comprise spacer members.

6. The method according to claim 1, wherein the tooth prosthesis system is designed to be applied to a patient in one or only a few days.

7. The method according to claim 1, further comprising:
providing the tooth-prosthesis-supporting part with a shape having a narrower horizontal cross section than the shape of the bearing part; and forming the bearing part and the tooth prosthesis supporting part with one or more outside transitions that each form a curved or arc-shaped transition between the bearing part and the tooth prosthesis supporting part.

8. The method according to claim 7, wherein the bearing part and the tooth prosthesis supporting part are provided with their shapes at the time of manufacture.

9. The method according to claim 1, further comprising:
providing the bearing part with depressions at its surface that can cooperate with the fixtures, the depressions having plane bottom surfaces that are opposite the end surfaces of the fixtures; and providing the plane bottom surfaces of the depressions with surface areas that exceed the surface areas of the fixtures at the parts of the fixtures cooperating with the bearing parts.

10. The method according to claim 1, further comprising:
providing the tooth-prosthesis-supporting part with holes extending in a transverse direction.

11. The method according to claim 10, wherein tooth-prosthesis-supporting part is provided with the holes extending in a transverse direction at the time of its manufacture.

12. The method according to claim 1, wherein the bearing part and the tooth prosthesis-supporting part are made of a tissue-compatible material or tissue-compatible alloy.

13. The method according to claim 12, wherein the bearing part and the tooth prosthesis-supporting part are made of titanium or titanium alloy.

14. The method according to claim 1, further comprising:
designing the bearing part and the tooth prosthesis-supporting part with a similar low height.

15. The method according to claim 14, wherein the bearing part and the tooth prosthesis-supporting part have a height of between 0.5 and 1.0 mm.

16. The method according to claim 14, wherein the bearing part and the tooth prosthesis-supporting part have a height of between 0.7 and 0.8 mm.

17. The method according to claim 1, wherein producing the superstructure comprises:
- machining;
- at least one of grinding or barrel polishing of sharp edges; and
- production of outer bevels.

18. The method according to claim 1, wherein producing the superstructure comprises:
- casting a sinterable material to form the bearing part and the tooth prosthesis-supporting part;
- carrying out a sintering procedure or solidifying procedure; and
- working of an outer shape to give user-friendliness.

19. The method according to claim 1, further comprising:
- providing or covering a front end of the superstructure with material forming the tooth prosthesis.

20. The method according to claim 19, wherein the material providing or covering a front end of the superstructure comprises acrylate or another synthetic material used in tooth prostheses.

21. The method according to claim 1, wherein the recesses for the securing members have diameters that are only slightly less than the width of the prosthesis supporting part.

22. A superstructure arrangement for use in a tooth prosthesis system together with fixtures and securing members for anchoring the superstructure in the fixtures, the tooth prosthesis system being designed to apply a complete tooth prosthesis to dentine in a short application time, the superstructure comprising:
- a unitary member comprising a bearing part operative to cooperate with the fixtures and a tooth-prosthesis-supporting part; and
- continuous recesses through the bearing part and the tooth-prosthesis-supporting-part operative to receive the securing members,
- wherein the superstructure has an arc shape, wherein at the ends of the arc shape the bearing part comprises a first bevel that merges via a curved part into a lower surface of the tooth-prosthesis-supporting part, wherein the lower surface of the tooth-prosthesis-supporting part is curved up toward an outer edge of the tooth-prosthesis-supporting part via a second bevel.

23. The superstructure arrangement according to claim 22, wherein the superstructure is operative to work without being included in the covering function for the exposed end surfaces of implanted fixtures and is operative to be removed from the fixtures during application of the tooth prosthesis to the superstructure.

24. The superstructure arrangement according to claim 22, wherein the bearing part is operative to cooperate with fixtures that comprise spacer members.

25. The superstructure arrangement according to claim 22, wherein the tooth prosthesis system is operative to be applied to a patient in one or only a few days.

26. The superstructure arrangement according to claim 22, wherein the bearing part cooperates with at least one of fixtures or fixture parts with cutting edges at their front parts that provide a direction-ensuring function during screwing into the dentine, irrespective of the homogeneity of the latter.

27. The superstructure arrangement according to claim 22, wherein the bearing part is provided with depressions with plane bottom surfaces via which the bearing part lies against the top surfaces of the fixtures.

28. The superstructure arrangement according to claim 22, wherein the tooth-prosthesis supporting part is provided with a shape having a horizontal cross section that is narrower than the horizontal cross section of the bearing part, and wherein the bearing part and the tooth prosthesis supporting part are formed with one or more outside transitions that form a curved or arc-shaped transition between the parts.

29. The superstructure arrangement according to claim 22, wherein the bearing part further comprises depressions arranged on a surface cooperating with the fixtures, the depressions having plane bottom surfaces that are opposite free end surfaces of the fixtures, the plane bottom surfaces of the depressions having surface areas that exceed the surface areas of the fixtures at parts of the fixtures cooperating with the bearing part.

30. The superstructure arrangement according to claim 22, wherein the tooth prosthesis-supporting part is provided with holes extending in a transverse direction.

31. The superstructure arrangement according to claim 22, wherein the bearing part and the tooth prosthesis-supporting part are made of a tissue-compatible material or tissue-compatible alloy.

32. The superstructure arrangement according to claim 31, wherein the bearing part and the tooth prosthesis-supporting part are made of titanium or titanium alloy.

33. The superstructure arrangement according to claim 22, wherein the bearing part and the tooth prosthesis-supporting part have a similar low height.

34. The superstructure arrangement according to claim 33, wherein the bearing part and the tooth prosthesis-supporting part have a height of between 0.5 and 1.0 mm.

35. The superstructure arrangement according to claim 33, wherein the bearing part and the tooth prosthesis-supporting part have a height of between 0.7 and 0.8 mm.

36. The superstructure arrangement according to claim 22, wherein the superstructure comprises front parts, wherein at the front parts the superstructure is arranged such that it can be covered by material forming the tooth prosthesis.

37. The superstructure arrangement according to claim 22, wherein the recesses for the securing members have diameters that are only slightly less than a width of the tooth prosthesis-supporting part.

* * * * *